United States Patent
Axon et al.

(10) Patent No.: US 7,323,152 B2
(45) Date of Patent: Jan. 29, 2008

(54) CATALYST OR SORBENT BEDS

(75) Inventors: Sean Alexander Axon, Cleveland (GB); Andrew Mark Ward, Cleveland (GB); Alan Bruce Briston, Cleveland (GB)

(73) Assignee: Johnson Matthey PLC, London (GB)

( * ) Notice: Subject to any disclaimer, the term of this patent is extended or adjusted under 35 U.S.C. 154(b) by 384 days.

(21) Appl. No.: 10/485,049

(22) PCT Filed: Jul. 3, 2002

(86) PCT No.: PCT/GB02/03075

§ 371 (c)(1), (2), (4) Date: Jun. 29, 2004

(87) PCT Pub. No.: WO03/011448

PCT Pub. Date: Feb. 13, 2003

(65) Prior Publication Data
US 2004/0234433 A1 Nov. 25, 2004

(30) Foreign Application Priority Data
Jul. 27, 2001 (GB) ................. 0118322.7

(51) Int. Cl.
B01J 8/02 (2006.01)
B01D 53/50 (2006.01)

(52) U.S. Cl. .................. 423/240 R; 422/216; 422/218; 422/221; 422/211; 423/242.1; 423/244.02

(58) Field of Classification Search ............... 422/241, 422/211, 216, 218, 221; 502/439, 527.1; 423/240 R, 242.1, 244.02
See application file for complete search history.

(56) References Cited

U.S. PATENT DOCUMENTS

| 3,909,208 A | 9/1975 | Boret et al. |
| 4,314,914 A | 2/1982 | Uede et al. |
| 4,814,147 A | 3/1989 | Flork |
| 5,710,089 A * | 1/1998 | Khare ................ 502/407 |
| 5,882,385 A | 3/1999 | Bosquain et al. |

FOREIGN PATENT DOCUMENTS

| EP | 0 798 798 A3 | 10/1997 |
| GB | 2 157 671 A | 10/1985 |
| JP | 59-59244 | 4/1984 |
| WO | WO-98/28073 | 7/1998 |

OTHER PUBLICATIONS

International Search Report dated Oct. 21, 2002, from International Application No. PCT/GB02/03075.
British Search Report dated Feb. 8, 2002, from British Application No. GB 0118322.7.

* cited by examiner

Primary Examiner—N. Bhat
(74) Attorney, Agent, or Firm—RatnerPrestia

(57) ABSTRACT

A fixed bed containing a particulate catalyst or sorbent material (10) subject to operation at high temperature having a shaped boundary member (16) inclined to the direction of fluid flow through the bed that maintains the depth of said catalyst or sorbent at the boundary of the bed through a series of thermal expansion-thermal contraction cycles is described. By maintaining bed depth, the shaped boundary member (16) can prevent bypass of, e.g. ammonia through a bed of particulate ammonia oxidation catalyst.

12 Claims, 2 Drawing Sheets

CATALYST OR SORBENT BEDS

This application is the U.S. National Phase Application of PCT International Application No. PCT/GB02/03075.

This invention relates to fixed beds of catalyst or sorbent and in particular, in order to increase the effectiveness of the bed, to means for maintaining the depth of the bed through a series of thermal expansion-thermal contraction cycles.

A fixed bed generally comprises at least one layer of a catalyst or sorbent in the form of a particulate material such as extrudates, pellets or granules bounded by a process fluid-impermeable boundary member and disposed on a perforate member, for example a perforate plate, grid or mesh through which a process fluid passing through the bed may pass. The bed is disposed within a vessel wherein it is supported directly by the vessel wall by means of, e.g. lugs, or by process fluid-impermeable bed supporting means such as a basket or framework attached to the vessel wall.

The boundary member may or may not be fixed to the perforate member. However, the boundary member is typically parallel to the direction of fluid flow through the bed and prevents the particles contacting with the wall of the vessel in which the bed is disposed. Where the bed is subjected to elevated temperatures, such a boundary member may be described as a heat shield as it protects the vessel wall or bed supporting means from the particulate catalyst or sorbent at high temperature.

It is preferred that the flow of gas or liquid through the bed of catalyst or sorbent is uniform to provide consistent operation in terms of conversion in the case of a catalyst bed, or absorption in the case of an absorbent bed. To achieve this generally the size of the particles and particularly the thickness of the layer of particles is carefully controlled to achieve a uniform permeability through the bed, through which the process fluid may flow. This is especially important in thin fixed beds, i.e. beds having a depth less than the vessel diameter.

A problem encountered with fixed beds containing particles of catalyst or sorbent and in particular thin fixed beds subjected to high temperatures is that where the particles make contact with the boundary member it has been found that the thermal expansion and contraction of the bed associated, e.g. with start-up-shutdown procedures can result in a reduction in the bed depth, particularly in the region where the bed contacts with the boundary member. Consequently, the gas-flow path through the bed is shorter near the boundary member and hence the flow of gas or liquid through the bed, i.e. permeability, is higher in this region.

This increase in flow through the bed reduces the contact time between fluid and catalyst or sorbent and may result in the problem of fluid by-pass. In the case of a catalytic process where substantially 100% conversion is required, this can result in unreacted species entering the product stream and in the case of a sorbent bed, similarly requiring substantially complete removal of contaminants, this can result in the undesirable presence of contaminants in any downstream process and/or the product.

We have found that the use of a shaped boundary-member can maintain the thickness of the bed through a series of thermal expansion-thermal contraction cycles and hence reduce the problem of by-pass.

Accordingly, the present invention provides a fixed bed through which a process fluid may flow comprising a particulate material disposed on a perforate member and bounded by a process fluid impermeable boundary member wherein at least a part of said boundary member bounds said particulate material for at least substantially the depth of the bed at an overall angle between 20 and 70 degrees to the direction of fluid flow through said bed.

In the present invention the fixed bed may be subjected to axial and/or radial flow of the process fluid which may be gaseous or liquid. Preferably, the bed of the present invention is subject to axial flow and may be disposed, for example, substantially horizontally in the vessel with process fluid passing substantially vertically through the bed.

The bed comprises particles of catalyst or sorbent disposed on a perforate member such as a perforate plate, mesh or grid having appropriately-sized holes to prevent passage of the particles therethrough. An inert particulate material may also be present, for example as a support layer underneath the catalyst or sorbent which forms part of the depth of the bed. The bed is bounded by a continuous, process fluid impermeable boundary member. The bed may be supported by the vessel wall via the perforate member or boundary member, e.g. by means of lugs attached to the vessel wall or alternatively by a basket, cradle or framework attached to the vessel wall. Preferably, the bed is supported via the perforate member by a process fluid-impermeable basket or framework attached to the vessel wall. Such means vary depending upon the type of bed, vessel and process and may be termed, "bed supporting means". The bed may be of any shape necessary to provide the required task. Often the bed shape matches that of the cross-section of the vessel in which it is disposed. For example, the bed may be circular, oval, square, rectangular, hexagonal or octagonal. The bed width may be in the range of 0.25 m to 6 m and is preferably 0.5 m to 3.5 m.

The present invention is of particular utility where the bed is relatively thin, i.e. having a depth less than the vessel diameter. Preferably the bed of the present invention has a depth between 5 and 500 mm, more preferably between 25 and 300 mm and most preferably between 25 and 100 mm.

The particles of catalyst or sorbent or inert particulate support material (if present) are in the form of spheres, platelets, cubes, extrudates, cylindrical pellets, granules or other regular or irregular shapes, generally having an aspect ratio, i.e. the largest dimension divided by the smallest dimension, of less than 2. The size of the particles may be uniform or different as required to create the desired contact time between gas or liquid and catalyst or sorbent.

The size and shape of the boundary member of the present invention will vary depending upon the size of the bed and the nature of the vessel wall or bed supporting means. The boundary member of the present invention may or may not be fixed to the perforate member supporting the bed. In a preferred embodiment, to reduce the effect of stresses due to thermal expansion and contraction of the bed, the boundary member is not fixed to the perforate member. In this embodiment, the boundary member will bound the particles of catalyst or sorbent such that the particulate material cannot pass through any remaining gap between the boundary member and perforate member, extend for at least substantially the depth of the bed and be attached to the vessel wall or bed supporting means, for example a basket that separately supports the perforate member at a suitable position, which may be above or below the surface of the bed. Alternatively, as stated above, the boundary member may be attached to the perforate member. Howsoever the boundary member is attached, it, and any bed supporting means should provide a process fluid-impermeable barrier around the periphery of the bed such that substantially all the process fluid is directed to pass through the particulate material disposed on the perforate member.

The boundary member extends from the perforate member for at least the depth of the bed and is inclined for the depth of the bed at an overall angle theta ($\theta$) between 20 and 70 degrees to the flow of fluid flow through the bed. If the overall angle is less than 20 degrees the bed depth may not be usefully maintained through a series of thermal expansion-thermal contraction cycles; if greater than 70 degrees then too large a part of the potential surface area of the bed may be taken up by the boundary member. Preferably the overall angle is between 20 and 60 degrees to the flow of fluid flow through the bed. By the term, "overall angle" we mean the angle between substantially the direction of fluid flow through the bulk of the bed and a straight line drawn between the lower end of the boundary member and the point where the boundary member meets substantially the upper surface of the bed. The boundary member comprises at least one facet extending from substantially the perforate member to the vessel wall or bed supporting means. Preferably the boundary member comprises between 1 and 50 facets. Each facet may be a variety of shapes, e.g. straight or curved and any combination of facets that provides an overall angle in the desired range may be used. It is preferable however that any combination of facets does not enclose particulate material or prevent process fluid from flowing through a substantial part of the particulate material in contact with the boundary member. Thus where a facet is curved, the lower end of the facet is preferably no greater than 90 degrees to the direction of fluid flow though the bed.

It has been found that a combination of facets that provides at least one step beneath the surface of the bed may improve the performance of the boundary member in maintaining the depth of the periphery of the bed through a series of thermal expansion and contraction cycles. By the term "step" we mean at least one straight or curved facet that extends a distance, e.g. a distance equivalent to between about 10 and 50% of the depth of the bed, into the bed at an angle greater than the angle of the facet immediately above it with respect to the direction of fluid flow through the bed. Preferably, between 1 and 10 steps may be provided. The steps may be the same or different sizes and the facets comprising different steps may be at the same or different angles to the direction of fluid flow through the bulk of the bed. In a preferred embodiment one step is provided and is preferably located at a depth between 25 and 75% of the depth of the bed. Preferably the step angle is about 90 degrees to the direction of fluid flow through the bulk of the bed.

The thickness of the boundary member will depend upon a number of factors including the dimensions of the vessel and/or bed but is preferably in the range of 1-25 mm, more preferably 1-10 mm.

The boundary member may be fabricated from any material suitable for use under the conditions of the catalytic or sorbent processes. Typically, the boundary member is fabricated from oxidation resistant alloys, for example 310 stainless steel.

The shaped boundary member of the fixed bed of the present invention with or without a step acts to maintain the thickness of the particulate material comprising the bed through a series of thermal expansion-thermal contraction cycles and thereby reduce the potential for by-pass of reactants or contaminants.

In an alternative embodiment the fixed bed comprises a particulate material bounded by a first outer boundary member as hereinbefore described extending from substantially the perforate member to a position above the surface of the bed, and a reservoir of particulate material, e.g. catalyst, sorbent or inert material, disposed between said first boundary member and a second inner boundary member extending from a position away from the perforate member beneath the surface of the bed to a position above the surface of the bed.

The second boundary member may be of any shape that suitably defines the reservoir of particulate material; e.g. facets above the surface of the bed may be aligned with the flow of fluid through the bed or may be parallel or angled away from the first boundary member. Preferably, the shape of the second boundary member within the bed is such that the it has an overall angle between 20 and 70 degrees to the direction of fluid flow through said bed to prevent the second boundary member effecting the thickness of the bed. The shape, the distance the first and second boundary members extend above the surface of the bed, and the spacing between them may be used to define the volume of the reservoir. Preferably the distance the first and second boundary members extend above the surface of the bed is between 5 and 300 mm and the closest distance between the first and second boundary members is preferably between 10 and 100 mm. Preferably the second boundary member extends beneath the surface of the bed to a depth less than 60% of the bed depth to reduce the possibility of the second boundary member effecting the thickness of the bed. The second boundary member is preferably fixed to the first boundary member by fixing means that allow flow of process fluid through the reservoir and into the bed, e.g. bolts, struts, spacer pins or plates aligned with the flow of process fluid through said reservoir. Preferably the reservoir is disposed such that the particles may pass to the bed under the force of gravity.

The thickness of the second boundary member will preferably be in the range of 1-25 mm, more preferably 1-10 mm and may be fabricated from the same materials as the first boundary member.

By forming a reservoir in this way the depth and hence the permeability of the periphery of the fixed bed may be controlled e.g. through a series of thermal expansion-thermal contraction cycles. The increased bed thickness between the first and second boundary members reduces permeability in this region and if particle shrinkage occurs, the volume of the bed may be maintained by particles of catalyst or sorbent from the reservoir.

As stated above, the fixed bed of the present invention may be a fixed catalyst bed. Preferably the catalyst may be any that is used disposed in thin beds. Processes that may utilise catalysts in thin beds include for example, ammonia oxidation using, e.g. a particulate cobalt-based catalyst, hydrodesulphurisation using e.g. a cobalt- or nickel-molybdate hydrodesulphurisation catalyst, formaldehyde manufacture using, e.g. a silver catalyst, hydrogen cyanide manufacture and partial oxidation reactions, for example for the partial oxidation of hydrocarbons as part of so-called 'gas-to-liquid' (GTL) processes. An inert particulate material such as alumina pellets may also be present, for example as a support layer underneath the catalyst. The particle size of the inert material may be the same or different from the particulate catalyst.

The fixed bed of the present invention may also be a fixed sorbent bed. By the term "sorbent" we necessarily include both adsorbent and absorbent materials. Any sorbent material suitable for the removal of sulphur, mercury, arsenic or compounds thereof, water and/or hydrogen chloride from process fluids, e.g. hydrocarbons, may be used. Examples of sorbent materials include basic zinc carbonate, manganese oxides and copper/zinc oxides for sulphur removal, copper sulphide for mercury and arsenic removal and sodium aluminate or lead carbonate for hydrogen chloride removal.

In particular the present invention is of utility where the bed is subjected to elevated temperatures. The bed temperatures are preferably greater than 100° C., more preferably greater than 200° C. and most preferably greater than 500° C.

BRIEF DESCRIPTION OF THE DRAWINGS

The invention will now be described with reference to the accompanying drawings in which;

In FIGS. 1, 2 and 3, the direction of flow of process fluid through the bulk of the bed, depicted by the arrow 'A', is substantially vertical in the direction of the arrow as illustrated. For clarity, line diagrams accompany FIGS. 1, 2 and 3 that represent the overall angle theta ($\theta$) between the direction of fluid flow through the bulk of the bed (A) and a straight line drawn between the lower end of the boundary member (C) and the surface of the bed (B).

Referring to the drawings, FIG. 1 shows a bed of catalyst e.g. for the oxidation of ammonia. The bed is provided by a layer of a cobalt-containing catalyst particles 10 on top of a layer of inert alumina particles 11 of e.g. larger size, disposed on a perforate member 12 having orifices 13 to allow the flow of gases through the bed. The bed is supported via the perforate member 12 which rests upon a lug 14 attached to a vessel wall 15.

Figure 1:
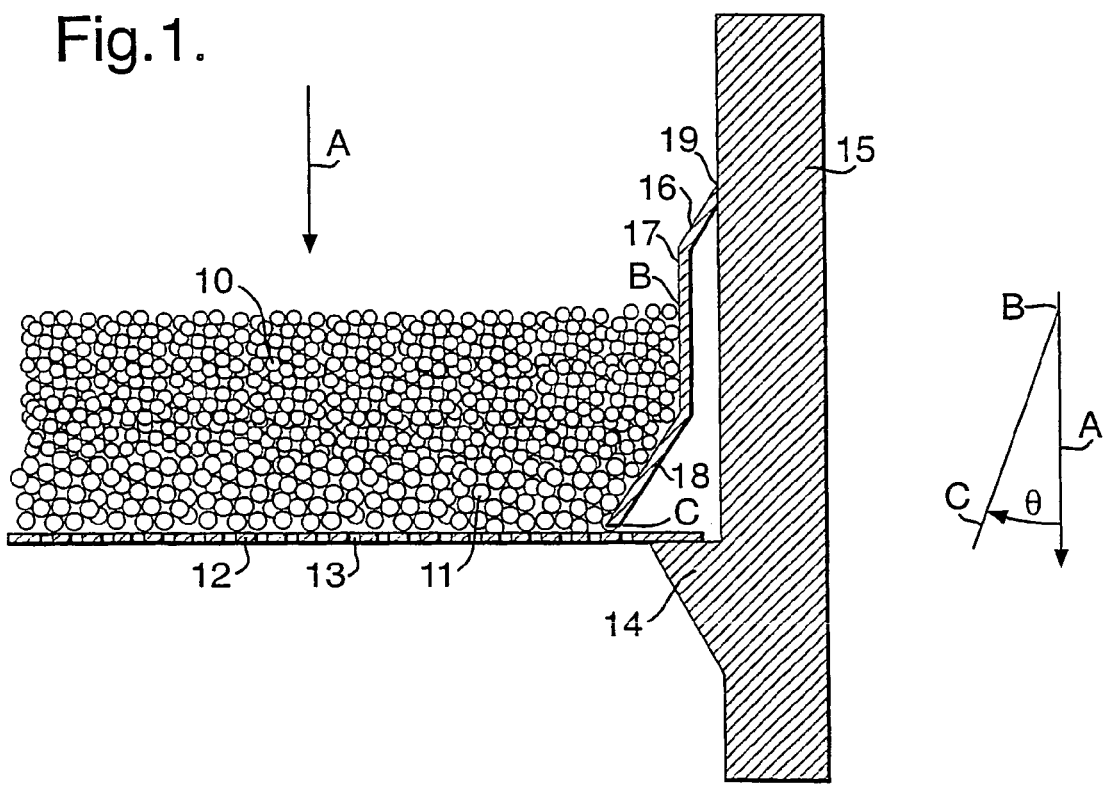
FIG. 1 is diagrammatic cross section of a boundary region of a circular fixed catalyst or sorbent bed in accordance with a first embodiment.
Figure 1:
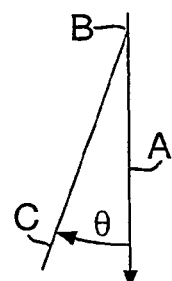

A boundary member comprising straight facets 16, 17 and 18 prevents the bed 10 from contacting the vessel wall 15. Facet 16 is attached to the vessel wall 15 at a point of attachment 19 above the bed and extends downwards towards the bed at an angle of about 30 degrees to a position approximately half way between the point of attachment 19 and the surface of the bed 10; facet 17 extends from the lower end of facet 16 at about 0 degrees, i.e. substantially parallel to the flow of process gas, beneath the surface of the bed to a depth approximately equivalent to 50% of the thickness of the bed; and facet 18 extends from the lower end of facet 17 to the perforate member 12 at an angle of about 35 degrees to the flow of fluid through the bed, to a depth corresponding to approximately 97% of the thickness of the bed. The overall angle, theta ($\theta$), of the boundary member (i.e. the angle between the direction of flow of process fluid through the bed, A, and the straight line drawn between points B-C) is about 20 degrees to the direction of fluid flow through the bed.

Figure 2:
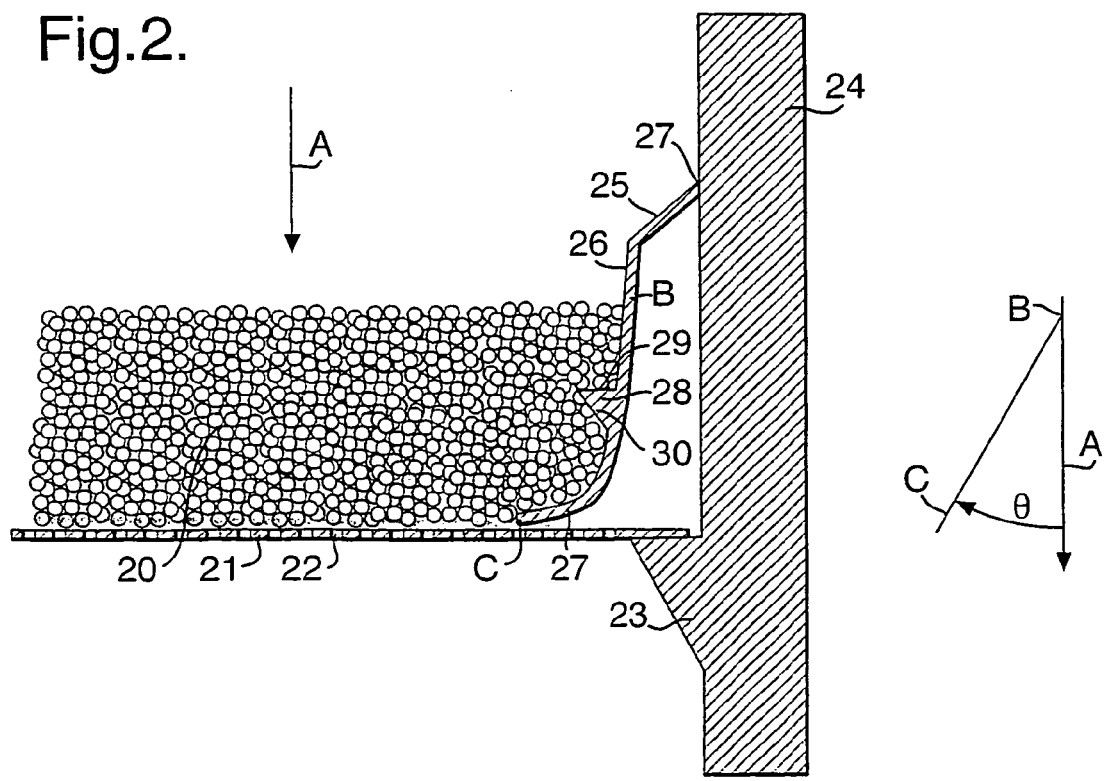
FIG. 2 is a diagrammatic cross section of a boundary region of a circular fixed catalyst or sorbent bed in accordance with a second embodiment.
Figure 2:
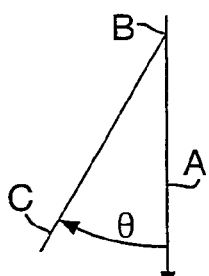

In FIG. 2 a bed of catalyst e.g. for the oxidation of ammonia is provided by a layer of a cobalt-containing catalyst particles 20 disposed on a perforate member 21 having orifices 22 to allow the flow of gases through the bed. The bed is supported via the perforate member 21 which rests upon a lug 23 attached to a vessel wall 24.

A boundary member comprising straight facets 25 and 26, and a curved facet 27 prevents the bed 20 from contacting the vessel wall 24. A step 28 is provided between the second straight facet 26 and the curved facet 27. The straight upper facet 25 extends from the vessel wall 24 from a point of attachment 27 above the bed 20 at an angle of about 50 degrees to the direction of fluid flow through the bed to a position approximately half way between the point of attachment 27 and the surface of the bed 20; facet 26 extends from the lower end of the straight upper facet 25 at an angle of about 5 degrees to a position corresponding to a depth of about 33% of the thickness of the bed; the step 28 comprises a first straight step facet 29 extending from the lower end of the upper straight facet 26 at an angle of approximately 90 degrees to the direction of fluid flow through the bed for a distance equivalent to about 15% of the thickness of the bed, and a second straight step facet 30 extending from the end of the first step facet 29 in a direction away from the bed for a distance approximately equal to the length of the first step facet at an angle of about 35 degrees. The curved facet 27 is attached to the end of the second step facet 30 and extends towards the bed at a chordal angle of about 45 degrees to a position corresponding to approximately 97% of the thickness of the bed. The overall angle theta ($\theta$) of the boundary member (i.e. the angle between the direction of flow of process fluid through the bed, A, and the straight line drawn between points B-C) is about 30 degrees to the direction of fluid flow through the bed.

Figure 3:
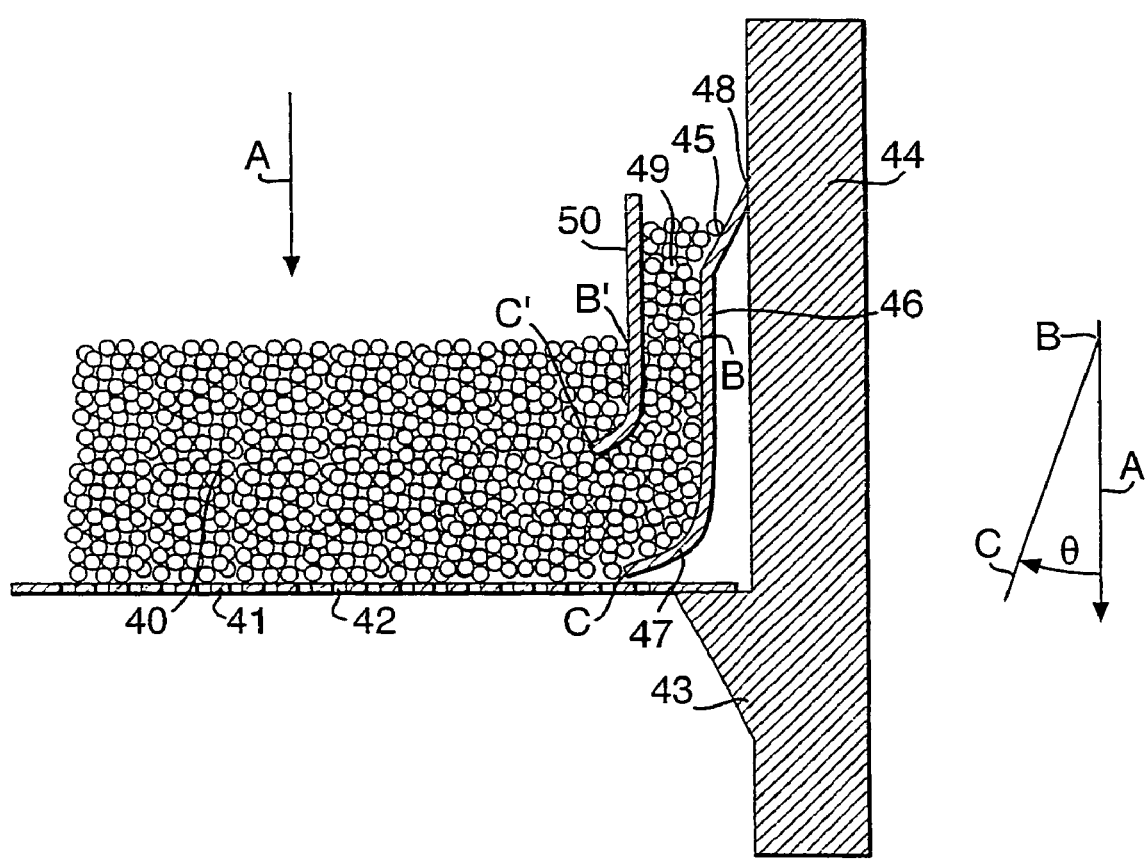
FIG. 3 is a diagrammatic cross section of a boundary region of a circular fixed catalyst or sorbent bed in accordance with a third embodiment.

In FIG. 3 a bed of catalyst e.g. for the oxidation of ammonia is provided by a bed of a cobalt-containing catalyst particles 40 disposed on a perforate member 41 having orifices 42 to allow the flow of gases through the bed. The bed is supported via the perforate member 41 which rests upon a lug 43 attached to a vessel wall 44.

A first boundary member comprising straight facets 45, 46 and curved facet 47 prevents the bed 40 from contacting the vessel wall 44. Facet 45 is attached to the vessel wall 44 at a point of attachment 48 above the bed and extends downwards towards the bed at an angle of about 30 degrees to a position approximately half way between the point of attachment 48 and the surface of the bed 40; facet 46 extends from the lower end of facet 45 at about 0 degrees, i.e. substantially parallel to the flow of process gas, beneath the surface of the bed to a depth approximately equivalent to 50% of the thickness of the bed; and curved facet 47 extends from the lower end of facet 46 towards the bed at a chordal angle of about 45 degrees to a position corresponding to approximately 97% of the thickness of the bed. The overall angle, theta ($\theta$), of the boundary member (i.e. the angle between the direction of flow of process fluid through the bed, A, and the straight line drawn between points B-C where B is level with the surface of the bulk of the bed) is about 20 degrees to the direction of fluid flow through the bed.

A reservoir of cobalt-containing catalyst particles 49 is disposed between the first boundary member and a second boundary member 50 extending from a point approximately level with the point of attachment 48 of said first boundary member into the bed to a position corresponding to approximately 50% of the thickness of the bed. The second boundary member is held in place by spacer struts fitted to the first boundary member (not shown). The second boundary member comprises a substantially vertical straight facet extending from above the surface of the bed to the surface of the bed and a curved facet extending into the bed from the lower end of the vertical facet towards the bed at a chordal angle of about 45 degrees. The reservoir has a depth equal to about 50% of the thickness of the bed and the second boundary member is spaced from said first member at a closest distance of about a quarter of the thickness of the bed. The overall angle of the second boundary member (i.e. the angle between the direction of flow of process fluid through the bed, A, and the straight line drawn between points B'-C') is also about 20 degrees to the direction of fluid flow through the bed.

In a preferred embodiment of the present invention a 50 mm deep catalyst bed of a cobalt-rare earth perovskite for the oxidation of ammonia at between about 800 and 900° C. as described in WO98/28073, disposed in a reactor of 0.5-6 m circular cross-section has a continuous circumferential boundary member extending from the bed supporting means towards the bed, comprising a straight upper facet and a curved lower facet and having a step extending into the bed between 5 and 15 mm, between said facets. The overall angle between the lower end of the curved facet and the point where the boundary member meets the surface of the bed is between 20 and 70 degrees to the direction of fluid flow though the bed. The catalyst particles are typically cylindrical pellets of 3 mm length and 3 mm diameter. They may be supported on a layer of $\alpha$-alumina pellets of typically 3-10 mm diameter of depth e.g. 25 mm. The boundary member maintains the bed thickness through a series of thermal expansion-thermal contraction cycles.

While the above embodiments are described in respect on an ammonia oxidation process, it will be understood that application of the fixed beds of the present invention may be applied to many processes, in particular processes utilising thin beds of catalyst or sorbent as hereinbefore described.

The invention claimed is:

1. A fixed bed through which a process fluid may flow, disposed in a vessel, said bed having a depth less than the diameter of the vessel and between 5 and 500 mm, comprising a particulate material disposed on a perforate member and bounded by a process fluid impermeable boundary member extending for at least substantially the depth of the bed wherein said boundary member is not fixed to the perforate member and at least a part of said boundary member bounds said particulate material for at least substantially the depth of the bed at an overall angle between 20 and 70 degrees to the direction of fluid through said bed.

2. A fixed bed according to claim 1 wherein the boundary member comprises between 1 and 50 curved and/or straight facets.

3. A fixed bed according to claim 2 wherein a combination of facets that provides at least one step beneath the surface of the bed is provided.

4. A fixed bed according to claim 1 having a first outer boundary member extending from substantially the perforate member to a position above the surface of the bed and a reservoir of particulate material disposed between said first outer boundary member and a second inner boundary member extending from a position away from the perforate member beneath the surface of the bed to a position above the surface of the bed.

5. A fixed bed according to claim 1 wherein the particulate material comprises a catalyst or sorbent.

6. A fixed bed according to claim 1 wherein the bed is subjected to temperatures greater than 100° C.

7. A process for the removal of materials containing sulphur, mercury, arsenic, water and/or hydrogen chloride from process fluids comprising the step of contacting said fluids with a fixed sorbent bed according to claim 1.

8. A process selected from the group consisting of ammonia oxidation, hydrodesulphurisation, hydrogen cyanide manufacture, formaldehyde manufacture or partial oxidation of hydrocarbons using a fixed catalyst bed according to claim 1.

9. A fixed bed according to claim 5 further comprising an inert material.

10. A fixed bed according to claim 1 wherein the boundary member comprises an upstream end fixed to a vessel wall and a downstream end extending into the bed that is free of attachment.

11. A fixed bed according to claim 1 wherein the boundary member comprises at least one step comprising a facet extending at an angle of about 90 degrees to the direction of the fluid flow through the bed.

12. A fixed bed through which a process fluid may flow, disposed in a vessel, said bed having a depth less than the diameter of the vessel and between 5 and 500 mm, comprising a particulate material disposed on a perforate member and bounded by a process fluid impermeable boundary member for at least substantially the depth of the bed wherein said boundary member comprises an upstream end fixed to a vessel wall and a downstream end free of attachment and at least a part of said boundary member bounds said particulate material for at least substantially the depth of the bed at an overall angle between 20 and 70 degrees to the direction of fluid flow through said bed, and wherein said boundary member further comprises at least one step comprising a facet extending at an angle of about 90 degrees to the direction of fluid flow through the bed.

* * * * *